(12) United States Patent
Lim et al.

(10) Patent No.: US 9,827,338 B2
(45) Date of Patent: Nov. 28, 2017

(54) GRP-R AGONISTIC 177-LUTETIUM-LABELED BOMBESIN DERIVATIVES FOR DIAGNOSIS AND TREATMENT OF PROSTATE CANCER

(71) Applicant: KOREA ATOMIC ENERGY RESEARCH INSTITUTE, Daejeon (KR)

(72) Inventors: Jae Cheong Lim, Sejong-si (KR); Eun Ha Cho, Daejeon (KR); Jin Joo Kim, Daejeon (KR); Sang Mu Choi, Daejeon (KR); So-Young Lee, Daejeon (KR); Ul Jae Park, Daejeon (KR); Sung Soo Nam, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 9 days.

(21) Appl. No.: 14/657,802

(22) Filed: Mar. 13, 2015

(65) Prior Publication Data

US 2016/0121004 A1 May 5, 2016

(30) Foreign Application Priority Data

Jun. 16, 2014 (KR) ........................ 10-2014-0072542

(51) Int. Cl.
| | |
|---|---|
| *A61K 51/08* | (2006.01) |
| *C07B 59/00* | (2006.01) |
| *A61K 49/10* | (2006.01) |
| *A61K 51/04* | (2006.01) |
| *C07K 14/575* | (2006.01) |

(52) U.S. Cl.
CPC ............. *A61K 51/08* (2013.01); *A61K 49/106* (2013.01); *A61K 51/0482* (2013.01); *A61K 51/088* (2013.01); *C07B 59/008* (2013.01); *C07K 14/57572* (2013.01)

(58) Field of Classification Search
None
See application file for complete search history.

(56) References Cited

FOREIGN PATENT DOCUMENTS

WO     2009143101 A2     11/2009

OTHER PUBLICATIONS

Hoffman et al. Novel series of 111In-labeled bombesin analogs as potential radiopharmaceuticals for specific targeting of gastrin-releasing peptide receptors expressed on human prostate cancer cells. J Nucl Med 2003; 44:823-831.*
Lantry, L. et al., "177Lu-AMBA: Synthesis and Characterization of a Selective 177Lu-Labeled GRP-R Agonist for Systemic Radiotherapy of Prostate Cancer," Journal of Nuclear Medicine, vol. 47, No. 7, Jul. 2006, 9 pages.
Lim, J. et al., "Novel Bombesin Analogues Conjugated with DOTA-Ala(SO3H)-4 Aminobenzoic Acid and DOTA-Lys (glucose)-4 Aminobenzoic acid: Synthesis, Radiolabeling, and Gastrin Releasing Peptide Receptor Binding Affinity," Journal of Radiation Industry, vol. 7, No. 2-3, Nov. 2013, 10 pages.

* cited by examiner

*Primary Examiner* — Satyanarayana R Gudibande
*Assistant Examiner* — Jia-Hai Lee
(74) *Attorney, Agent, or Firm* — McCoy Russell LLP

(57) ABSTRACT

Provided is a novel compound capable of being usefully used to diagnose and treat prostate cancer by labeling a radioisotope on a bombesin derivatives capable of selectively targeting a target material over-expressed in tumor cells in order to develop an effective diagnose and treatment method of diseases associated with prostate cancer.

8 Claims, 8 Drawing Sheets

FIG. 4

| Organ | 1 h[b] p.i. | 1 h p.i. | 2 h p.i. | 24 h p.i. |
|---|---|---|---|---|
| Blood | 0.25 ± 0.10 | 0.38 ± 0.23 | 0.07 ± 0.01 | 0.01 ± 0.01 |
| Liver | 0.31 ± 0.03 | 1.12 ± 0.87 | 0.20 ± 0.14 | 0.12 ± 0.05 |
| Kidney | 1.81 ± 0.24 | 3.36 ± 0.85 | 1.24 ± 0.24 | 0.85 ± 0.25 |
| Spleen | 0.38 ± 0.18 | 1.27 ± 0.37 | 0.39 ± 0.14 | 0.18 ± 0.02 |
| Heart | 0.10 ± 0.03 | 0.12 ± 0.03 | 0.06 ± 0.01 | 0.04 ± 0.02 |
| Pancreas | 0.65 ± 0.07 | 66.20 ± 5.71 | 34.98 ± 2.26 | 19.16 ± 1.31 |
| Small Intestine | 3.52 ± 1.77 | 8.47 ± 1.45 | 3.95 ± 0.93 | 0.65 ± 0.12 |
| Large Intestine | 0.30 ± 0.09 | 7.41 ± 0.38 | 1.83 ± 0.57 | 1.08 ± 0.21 |
| Lung | 0.38 ± 0.04 | 0.38 ± 0.06 | 0.18 ± 0.06 | 0.05 ± 0.02 |
| Stomach | 0.41 ± 0.16 | 3.01 ± 0.64 | 2.39 ± 0.20 | 0.58 ± 0.24 |
| Tumor | 0.90 ± 0.05 | 12.42 ± 2.15 | 7.55 ± 0.38 | 4.04 ± 0.47 |

[a]Results are expressed as % ID/g ± SD (n=3).
[b]Blockade study: animals received 50 μg of the peptide coinjected with the radiolabeled peptide.

FIG. 5

| | | |
|---|---|---|
| Tumor (%ID/g) | 177Lu-AMBA (Comparative Material) | 6.35 ± 2.23 (1 h p.i.) |
| | 177Lu-DOTA-gluBBN (Example 2) | 12.42 ± 2.15 (1 h p.i.) |
| Tumor/Blood | 177Lu-AMBA (Comparative Material) | 13.80 (1 h p.i.) |
| | 177Lu-DOTA-gluBBN (Example 2) | 32.68 (1 h p.i.) |

GRP-R AGONISTIC 177-LUTETIUM-LABELED BOMBESIN DERIVATIVES FOR DIAGNOSIS AND TREATMENT OF PROSTATE CANCER

CROSS-REFERENCE TO RELATED APPLICATIONS

This application claims priority under 35 U.S.C. §119 to Korean Patent Application No. 10-2014-0072542, filed on Jun. 16, 2014, in the Korean Intellectual Property Office, the disclosure of which is incorporated herein by reference in its entirety.

INCORPORATION BY REFERENCE OF ELECTRONICALLY SUBMITTED MATERIAL

Incorporated by reference in its entirety herein is a computer-readable amino acid sequence listing submitted herewith and identified as follows: 474 bytes ASCII (Text) file named "Substitute_Sequence_Listing_PLS15305," created Jan. 11, 2016.

TECHNICAL FIELD

The following disclosure relates to a novel gastrin-releasing peptide receptor (GRP-R) agonistic 177-lutetium-labeled bombesin derivatives for diagnosis and treatment of prostate cancer.

BACKGROUND

Prostate cancer, which is one of the most common cancers in Korea, is a very fatal disease in adult male. In the case in which prostate cancer is found at an early stage, it may be easy to treat prostate cancer by prostatectomy or local radiotherapy, but in the case in which prostate cancer metastasizes, a treatment success rate is significantly decreased. Therefore, early detection and an effective treatment method of prostate cancer are required.

As an existing anticancer therapy, anticancer chemotherapy and surgical treatment are general treatment methods. Anticancer chemotherapy has a lot of side effects on normal cells and a treatment duration time is long, such that quality of life for patients may be deteriorated. In addition, it is not easy to apply the existing surgical treatment to old patients, and the prognosis is significantly poor. Therefore, recently, targeted therapy capable of specifically diagnosing tumor cells and selectively treating only the tumor cells has been spotlighted, and various researches into target therapy have been conducted. Particularly, in targeted radiotherapy using a radioisotope, side effects are significantly decreased, and a treatment duration time is short as compared to anticancer chemotherapy, such that the targeted radiotherapy may be applied to old patients or terminal cancer patients.

Prostate cancer may be targeted using a gastrin-releasing peptide receptor (GRP-R (BB2, BRS-2)), which is a receptor specifically over-expressed in a cancer cell membrane. Therefore, research into targeted therapy using bombesin derivatives capable of selectively targeting GRP-R has been actively conducted (177Lu-AMBA: Synthesis and Characterization of a Selective 177Lu-Labeled GRP-R Agonist for Systemic Radiotherapy of Prostate Cancer, J. Nucl. Med. 2006; 47:1144-1152). However, in this targeted therapy, it is very important to have high therapeutic effect in addition to having excellent targeting efficiency to more accurately diagnose a disease. Therefore, the present researchers needed to develop better targeted radiotherapy having more excellent targeting efficiency on tumor as compared to the related art and found that in the case of using a target material having excellent target efficiency to prostate cancer as described above, radiotherapy capable of having more excellent targeting efficiency due to high specificity and more effectively treating prostate cancer may be developed, thereby completing the present invention.

Particularly, prostate cancer may be diagnosed and treated by conjugating the bombesin derivatives, which is an agonist of the GPR-P, with a radioisotope. In the target therapy as described above, the larger an amount of target material concentrated on a targeted tumor site, the higher an accurate diagnostic yield, and the higher the expected therapeutic effect. In addition, the smaller the amount of target material concentrated on normal tissue, the smaller the side effects.

DISCLOSURE

Technical Problem

An embodiment of the present invention is directed to providing a novel compound capable of being usefully used to diagnose and treat prostate cancer by labeling a radioisotope on bombesin derivatives capable of selectively targeting a target material over-expressed in tumor cells in order to develop an effective diagnosis and treatment method of the diseases associated with prostate.

Technical Solution

In one general aspect, there is provided a bombesin derivatives represented by the following Chemical Formula 1.

[Chemical Formula 1]

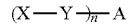

[In Chemical Formula 1,
n is an integer of 1 to 3,
X is a metal chelator,
Y is a spacer, and
A is a bombesin derivatives agonist represented by the following sequence.]
A: Gln-Trp-Ala-Val-Gly-His-Leu-Met-NH$_2$
X may include one or more radioactive metal nuclides and be a metal chelator for a trivalent metal and derivatives thereof.

The metal chelator for the trivalent metal may be a DOTA-based chelator or an derivatives thereof.

The radioactive metal nuclide may be for radiotherapy and be selected from the group consisting of $^{176}$Yb, $^{111}$In, $^{169}$Gd, $^{177}$Lu, $^{105}$Rh, $^{111}$Ag, $^{64}$Cu, $^{67}$Ga, $^{68}$Ga, $^{123}$I, $^{125}$I, $^{123}$I, $^{129}$I, and $^{166}$Ho.

The bombesin derivatives may be a compound represented by the following Chemical Formula 2.

[Chemical Formula 2]

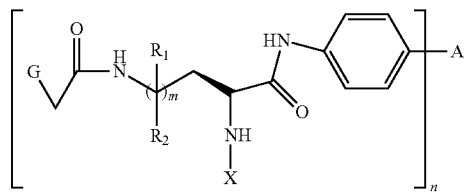

[In Chemical Formula 2, n is an integer of 1 to 3, m is an integer of 1 to 5, $R_1$ to $R_2$ are each independently hydrogen or (C1-C5) alkyl, and G is a glucose group or derivatives thereof.]

The spacer Y may be Lys(glucose)-4 aminobenzoic acid.

In another general aspect, there is provided a preparation method of bombesin derivatives including synthesizing a compound represented by the Chemical Formula 2.

[Chemical Formula 2]

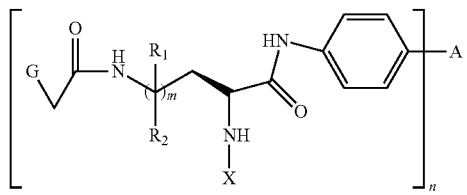

[In Chemical Formula 2, n is an integer of 1 to 3, m is an integer of 1 to 5,

X is a metal chelator, $R_1$ to $R_2$ are each independently hydrogen or (C1-C5) alkyl, A is *-Gln-Trp-Ala-Val-Gly-His-Leu-Met-NH2, G is a glucose group or derivatives thereof.]

In another general aspect, there is provided a composition for diagnosis and treatment of diseases associated with prostate, containing the bombesin derivatives as described above.

Advantageous Effects

The present invention relates to the bombesin derivatives capable of efficiently and selectively targeting prostate cancer over-expressing the GRP-R. As tumor targeting efficiency is increased by using the bombesin derivatives, it is possible to expect more accurate diagnosis and higher therapeutic effect.

In addition, the material provided in the present invention has significantly excellent tumor targeting efficiency as compared to a bombesin derivatives according to the related art, having similar mechanism, and it is possible to perform significantly accurate imaging diagnosis and treatment due to characteristics of the radioisotope 177-Lu emitting beta and gamma energy.

Therefore, the material provided in the present invention may be more usefully used to diagnose and treat prostate cancer over-expressing GRP-R.

DESCRIPTION OF DRAWINGS

FIG. 4 is a table showing in vivo distribution patterns of 177Lu-DOTA-gluBBN in a tumor mouse model xenografted with human prostate cancer PC-3 cells.

FIG. 5 is a table showing a comparison result of in vivo targeting efficiency to prostate cancer with a comparative material having a mechanism similar to that of 177Lu-DOTA-gluBBN.

DETAILED DESCRIPTION OF EMBODIMENTS

Figure 1:
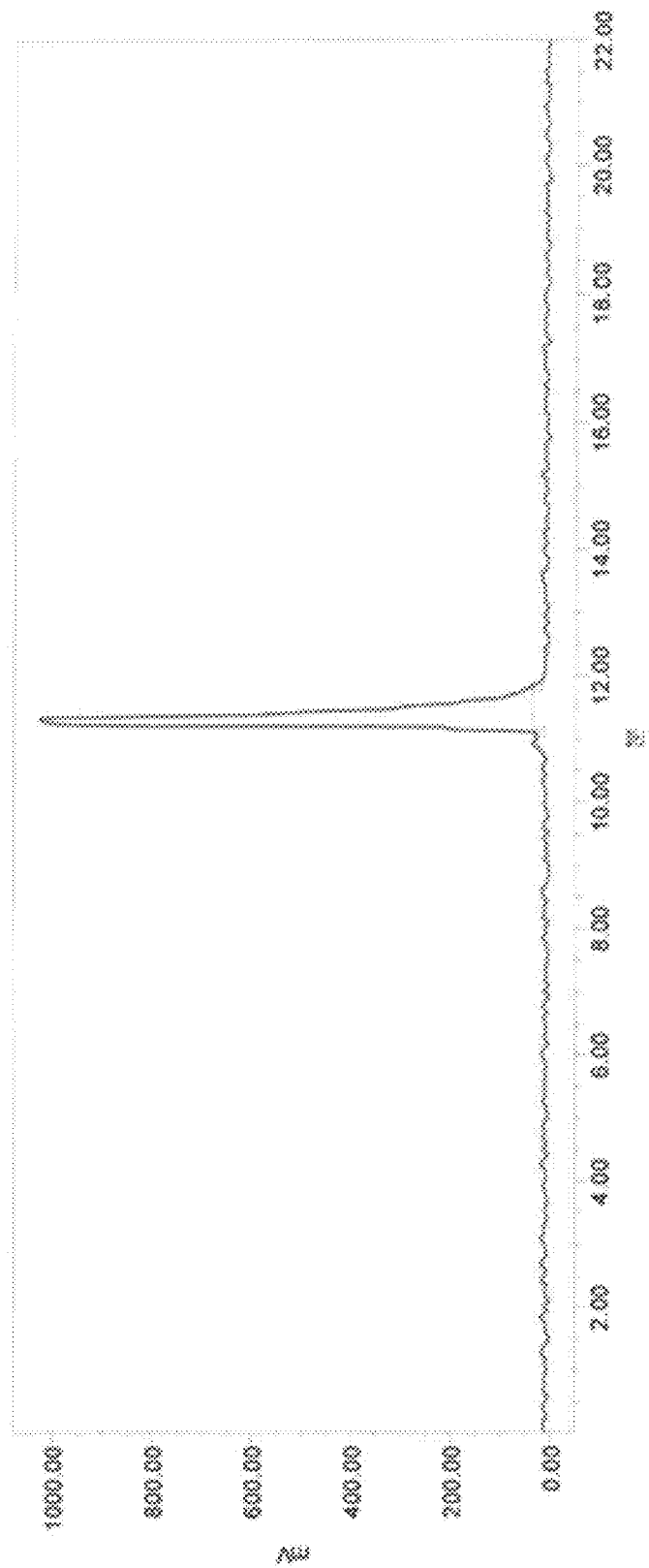
FIG. 1 is a graph showing purity at the time of preparing 177Lu-DOTA-gluBBN.

The present invention provides a bombesin derivatives capable of targeting GRP-R over-expressed in prostate cancer.

According to the present invention, novel bombesin derivatives may be represented by the following Chemical Formula 1.

[Chemical Formula 1]

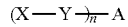

[In Chemical Formula 1, n is an integer of 1 to 3,

X is a metal chelator,

Y is a spacer, and

A is a bombesin derivatives agonist represented by the following sequence.]

A: Gln-Trp-Ala-Val-Gly-His-Leu-Met-NH2

According to an exemplary embodiment of the present invention, there is provided a novel and improved compound for imaging diagnosis and radiotherapy of prostate cancer.

In Chemical Formula 1, it is most preferable that n is 1.

The compound may include the metal chelator. The compound includes an optical label portion capable of being synthesized by chelating a medically useful metal ion or radioactive nuclide with a GRP-R targeted peptide having a bombesin derivatives agonist sequence by a linker or a spacer group.

The metal chelator means a molecule forming a complex with a metal atom. In this case, the complex is stable under physiological conditions. More specifically, the metal chelator may be a molecule synthesized with a radioactive metal nuclide to thereby be physiologically stable and having at least one reactive functional group for conjugation with the spacer. In addition, the metal chelator may include a single amino acid between the metal chelator and the spacer in order to bind to the spacer.

The metal chelator may be a metal chelator including one or more radioactive metal nuclides and be a metal chelator for a trivalent metal and derivatives thereof.

Preferably, the metal chelator for the trivalent metal may be a DOTA-based chelator and derivatives thereof. Most preferably, the chelator used in the compound according to the present invention may be a metal chelator represented by the following Chemical Formula 4.

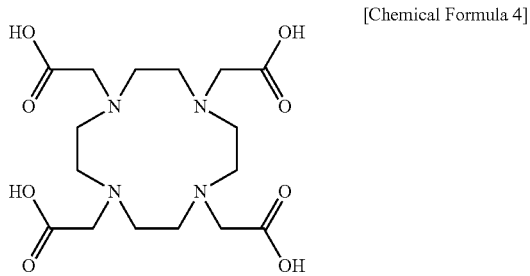 [SMILES: O=C(O)CN1CCN(CC(=O)O)CCN(CC(=O)O)CCN(CC(=O)O)CC1]

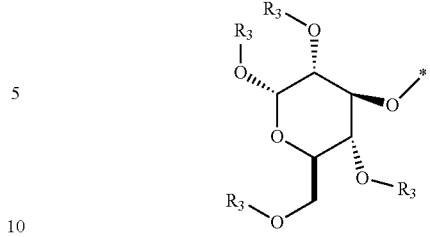

It is most preferable that $R_3$ is hydrogen.

According to an exemplary embodiment of the present invention, the spacer may include at least one amino acid. For example, it is most preferable that the amino acid is, for example, lysine (Lys).

A most preferable spacer used in the bombesin derivatives of the present invention may be Lys(glucose)-4 aminobenzoic acid and be represented by the following Chemical Formula 3.

The metal chelator may include one or more radioactive metal nuclides, wherein preferable examples of the radioactive metal nuclide for imaging diagnosis and radiotherapy include $^{64}$Cu, $^{67}$Ga, $^{68}$Ga, $^{111}$In, $^{105}$Rh, $^{176}$Yb, $^{169}$Gd, $^{177}$Lu, $^{111}$Ag, $^{125}$I, $^{129}$I, and $^{166}$Ho. The radioactive metal nuclide may be selected by diagnosis or therapy application, and particularly, $^{177}$Lu is preferable.

The bombesin derivatives according to the present invention includes a newly improved spacer capable of linking an optical marker synthesized with the radioactive metal nuclide to the GRP-R targeted peptide having the bombesin derivatives agonist sequence.

The spacer according to the present invention is represented by the following Chemical Formula 2.

[Chemical Formula 3]

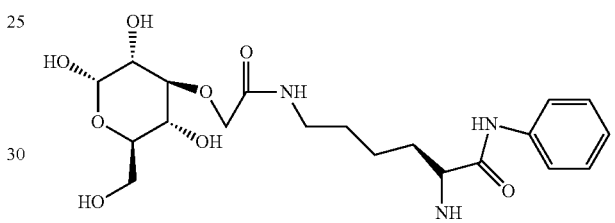

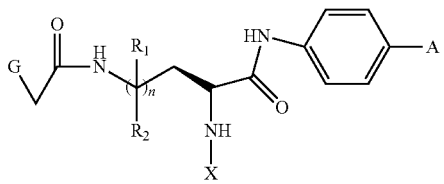

[Chemical Formula 2]

[In Chemical Formula 2, n is an integer of 1 to 5;

$R_1$ to $R_2$ are each independently hydrogen or (C1-C5) alkyl, and

G is a glucose group or derivatives thereof.]

The spacer may be used to serve to link the metal chelator including the radioactive metal nuclide and the GRP-R targeted peptide having the bombesin derivatives agonist sequence to each other.

According to an exemplary embodiment of the present invention, the spacer may be linked to A, which is a GRP-R targeted peptide having bombesin derivatives agonist sequence, to thereby link the metal chelator and the GRP-R targeted peptide having the bombesin derivatives agonist sequence.

Preferably, in the spacer used in the present invention, G may preferably include the glucose group G, wherein G is the glucose group or the derivatives thereof and may be represented by the following structure.

($R_3$(s) are each independently hydrogen or hydroxyl protecting group.)

The bombesin derivatives according to the present invention includes the bombesin derivatives agonist sequence (A in Chemical Formula 1 ((X—Y—)$_n$A)), which is the GRP-R targeted peptide.

The GRP-R, which is a receptor of gastrin releasing peptide (GRP) corresponding to a kind of peptide having physiological activity such as gastrin secretion promoting activity, pancreatic enzyme secretion promotion activity, cell proliferation activity, and the like, is a peptide known that the GRP-R is specifically over-expressed in a prostate cancer cell membrane and may be used as a target peptide of prostate cancer.

Therefore, the bombesin derivatives agonist, which is the GRP-R targeted peptide, serves as a GRP-R agonist. The bombesin derivatives agonist binds to the GRP-R that is over-expressed in the cancer membrane with high affinity to thereby activate cells and be uptaken in the cells.

The bombesin derivatives agonist, which is a bombesin inductive material for targeting the GRP-R of prostate cancer, may be formed by binding several amino acids. According to the present invention, it is most preferable that the bombesin derivatives agonist has a sequence of Gln-Trp-Ala-Val-Gly-His-Leu-Met-NH2.

The bombesin derivatives agonist is linked to a C-terminal of the spacer.

According to an exemplary embodiment of the present invention, the bombesin derivatives agonist, which is the GRP-R agonist, may be used to diagnose and treat prostate cancer by conjugating the radioisotope with the bombesin derivatives or derivatives thereof.

According to another exemplary embodiment of the present invention, there is provided a preparation method of a bombesin derivatives represented by the following Chemical Formula 1. More particularly, there is provided a preparation method of a bombesin derivatives including synthesizing a compound represented by the following Chemical Formula 2.

[Chemical Formula 1]

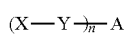

[In Chemical Formula 1,
n is an integer of 1 to 3,
X is a metal chelator,
Y is a spacer, and
A is a bombesin derivatives agonist represented by the following sequence.]
A: *-Gln-Trp-Ala-Val-Gly-His-Leu-Met-NH$_2$

[Chemical Formula 2]

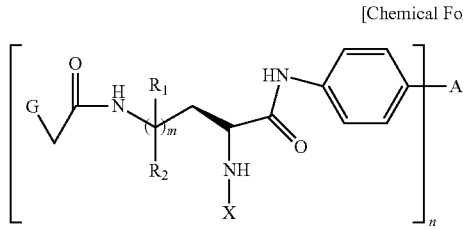

[In Chemical Formula 2,
n is an integer of 1 to 3,
m is an integer of 1 to 5,
X is a metal chelator,
$R_1$ to $R_2$ are each independently hydrogen or (C1-C5) alkyl,
A is *-Gln-Trp-Ala-Val-Gly-His-Leu-Met-NH2, and
G is a glucose group or derivatives thereof]

More specifically, in Chemical Formula 1, it is most preferable that n is 1.

In the preparation method of bombesin derivatives according to the present invention, the bombesin derivatives may be most easily prepared by solid-phase synthesis. More particularly, the bombesin derivatives may be prepared by solid-phase peptide synthesis that is generally established to thereby be widely used for binding peptide in the art. The solid-phase peptide synthesis includes adding stepwise an amino acid residue to a peptide chain connected to and growing on an insoluble supporter or polystyrene. First, a C-terminal residue of the peptide is protected by a N-protector, a t-butyloxycarbonyl (Boc) group, or a fluorenylmethoxycarbonyl (Fmoc) group. In the case in which the amino protecting group is the Fmoc group, the amino acid protecting group is removed by piperidine. Then, the amino acid residue (N-protected form) is added together with a coupling agonist, for example, HBTU.

Thereafter, the spacer according to the present invention may form a conjugate by reacting an amino group of a Gln residue of the bombesin derivatives agonist with a functional group of the spacer to thereby be coupled to each other.

The bombesin derivatives represented by Chemical Formula 1 may be finally prepared by reacting the metal chelator including a radioactive nuclide with the bombesin derivatives agonist binding to the spacer. The reaction may be performed by a chelation reaction known in the art, and the chelator including the radioactive nuclide may be labeled on the bombesin derivatives agonist through the chelation reaction as described above. Finally, the bombesin derivatives (hereinafter, referred to as '177Lu-DOTA-gluBBN') may be prepared.

The present invention provides a composition for diagnosis and treatment of diseases associated with the prostate, containing the bombesin derivatives.

The present invention provides the bombesin derivatives improved by the preparation method as described above, such that in a targeted therapy field such as a radioactive imaging diagnosis, radiotherapy, and the like, which are useful in diagnosis or treatment, the bombesin derivatives may be used to diagnose and treat prostate cancer in which the GRP-R is over-expressed in the cancer cell membrane.

At the time of applying targeted therapy using the improved bombesin derivatives prepared according to the present invention, since an amount of bombesin derivatives concentrate on a target tumor site, a higher therapeutic effect may be expected. On the other hand, bombesin derivatives concentrated on normal tissue is small, such that at the time of treatment, side effects may be decreased. In addition, the amount of bombesin derivatives concentrated on the target tumor site is large, which means that a large amount of bombesin derivatives may be concentrated even on a tumor site having a small size at the time of diagnosing leisons, such that imaging diagnosis of cancer lesions may be more accurately performed. In addition, since the bombesin derivatives according to the present invention serves as the GRP-R agonist, as described above, the bombesin derivatives may bind to the GRP-R peptide with high affinity to thereby be uptaken in cells. As described above, since the bombesin derivatives binds to tumor cells in the body to thereby be uptaken, the bombesin derivatives may be significantly effective to target prostate cancer cells over-expressing the GRP-R to thereby perform imaging diagnosis of prostate cancer.

The targeted therapy using the bombesin derivatives may be applied to a drug containing the bombesin derivatives together with a chemotherapeutic agent used in chemotherapy for diagnosing and treating cancer.

As the chemotherapeutic agent capable of being used to diagnose and treat cancer, any material may be used as long as it may simultaneously serve as a diagnostic and a therapeutic agent. As the chemotherapeutic agent, an anticancer agent used in this field may be used. More preferably, a monoclonal antibody capable of binding to an antigen of a cancer species may be used and applied to diagnose and treat cancer.

The bombesin derivatives according to the present invention may be administered to a patient together with the therapeutic agent as an ingredient of a composition containing an excipient, a diluent, a stabilizer, and a carrier that are widely known to be used in the art.

Hereinafter, the present invention will be described in more detail based on the following Examples. However, the following Examples are for illustrative purpose only, but the present invention is not limited thereto.

EXAMPLE 1

Synthesis of Bombesin Derivatives
(DOTA-gluBBN)

bombesin derivatives (DOTA-gluBBN) according to the present invention was prepared by solid-phase synthesis as shown in the following Reaction Formula.

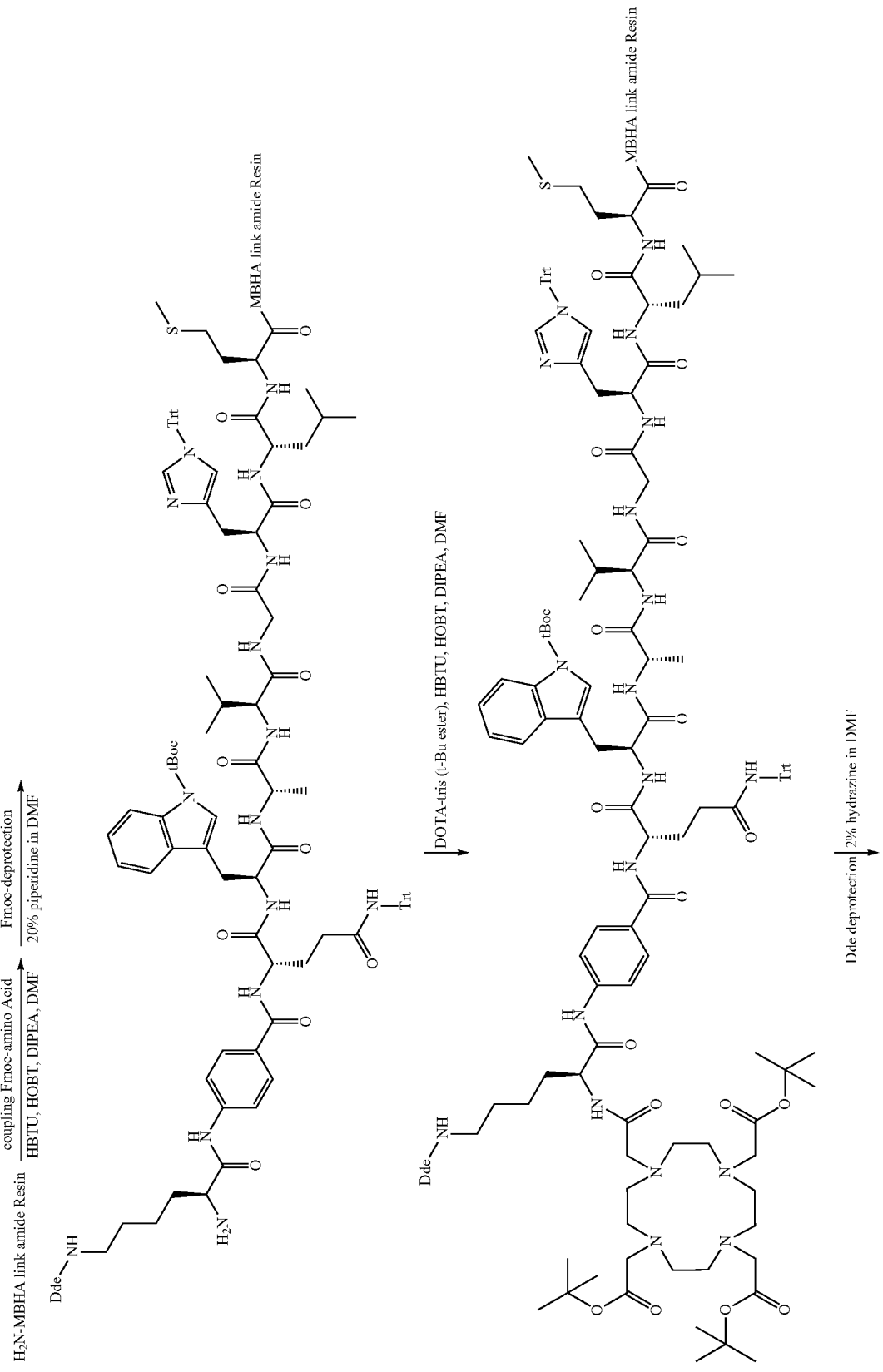

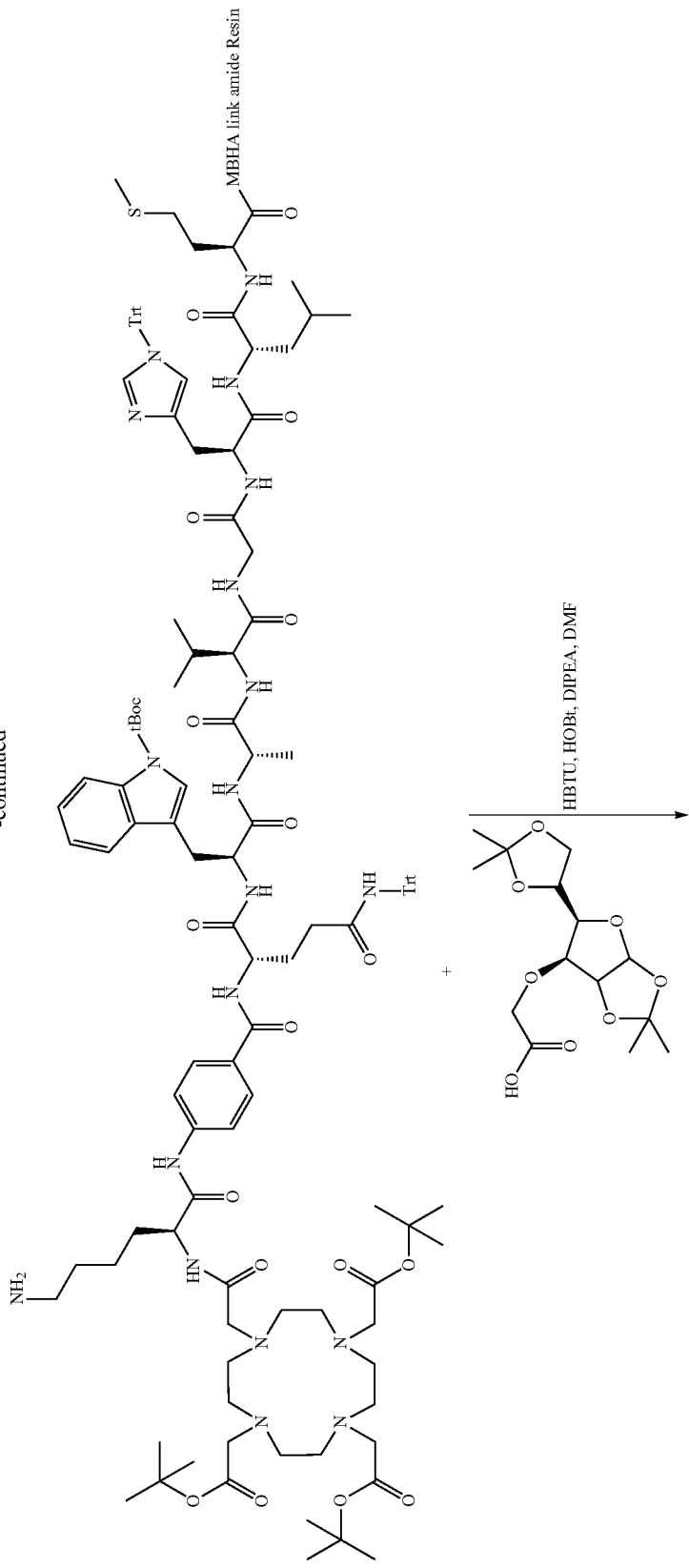

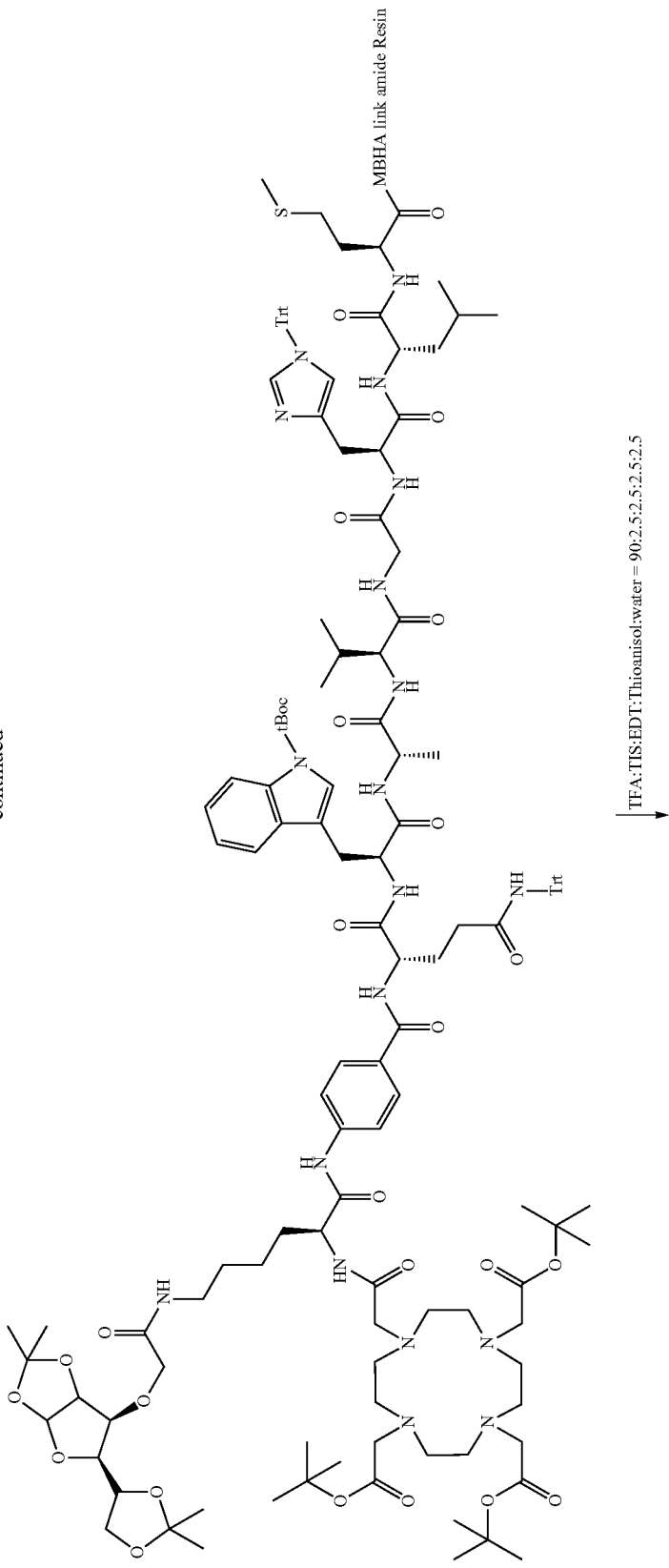

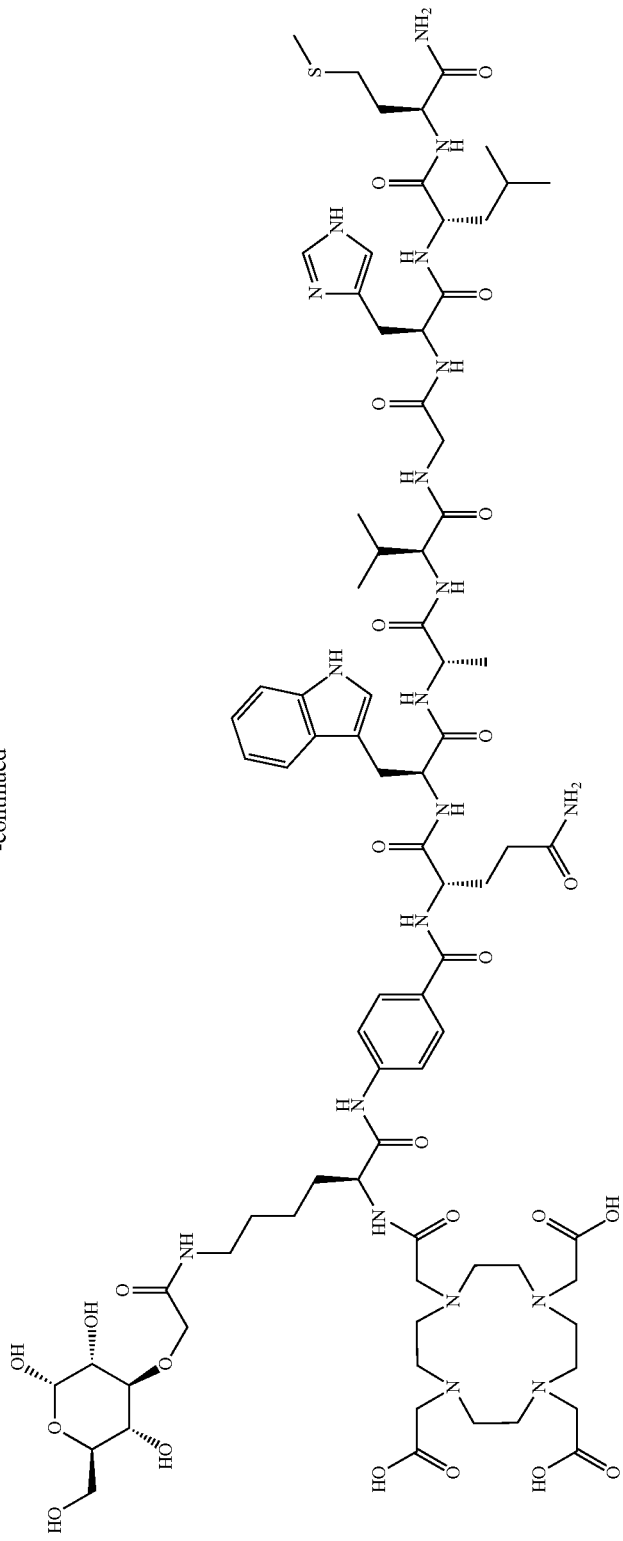

EXAMPLE 2

Preparation and Targeting Efficiency of 177Lu-DOTA-gluBBN

DOTA-gluBBN may be labeled using 177Lu with a high purity of 98% or more, and the result was shown in FIG. 1.

EXAMPLE 3

In Vitro Targeting Efficiency to Prostate Cancer (1) Cell Culture

In order to confirm in vitro targeting efficiency of DOTA-gluBBN and 177Lu-DOTA-gluBBN prepared according to Examples 1 and 2 to prostate cancer cells, PC-3 cells were used as a human prostate cancer cell line. The PC-3 cells corresponding to the human prostate cancer cell line were purchased from Korean cell line bank. The PC-3 cells were cultured in a Roswell Park Memorial Institute (RPMI) 1640 medium containing 10% fetal bovine serum (FBS) at 37° C. in 5% $CO_2$ atmosphere.

The cells were cultured in a disposable flask for cell culture, and at the time of an experiment, the cells were cultured in a 96-well or 12-well cell culture plate according to an experimental method and then used.

(2) In Vitro Targeting Efficiency of DOTA-gluBBN to Prostate Cancer Cell

Figure 2:
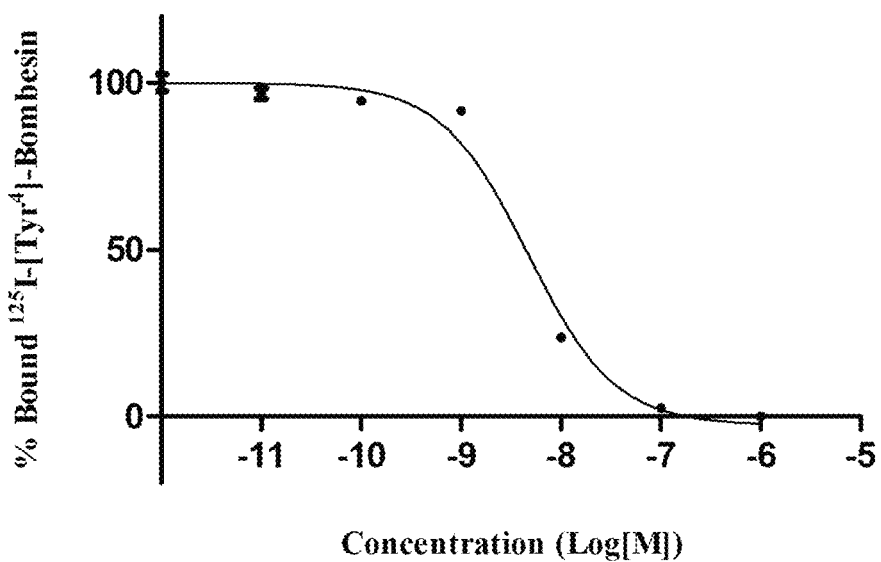
FIG. 2 is a graph showing a competitive binding curve with 125I-[Tyr4]-bombesin in human prostate cancer PC-3 cells.

DOTA-gluBBN ($10^{-6}$ to $10^{-12}$M) prepared according to Example 1 was co-cultured with 125I-[$Tyr^4$]-bombesin (20,000 CPM), respectively, in the PC-3 cells, which are human prostate cancer cells, to thereby carry out a competitive reaction. After culturing a cell plate at 37° C. for 1 hour, a reaction solution was recovered. After the cells were washed with PBS and recovered by 1N NaOH, radioactivity of each solution was measured using a gamma counter. A competitive binding curve with 125I-[$Tyr^4$]-bombesin was shown in FIG. 2. As a result, $IC_{50}$ was 4.67 nM, and DOTA-gluBBN had excellent targeting efficiency to the GRP-R at a nano molar level. The result was shown in FIG. 2.

In addition, 177Lu-DOTA-gluBBN (0.01 to 100 nM) prepared according to Example 2 was reacted, respectively, in the PC-3 cells. After culturing a cell plate at 37° C. for 2 hours, a reaction solution was recovered. After the cells were washed with PBS and recovered by 1N NaOH, radioactivity of each solution was measured using a gamma counter. As a result of analyzing the measured numerical value using a GraphPad Prism5 statistics program, a dissociation constant (Kd) value was about 0.63 nM, and 177Lu-DOTA-gluBBN had excellent targeting efficiency to the GRP-R at a nano molar level.

EXAMPLE 4

Internalization Characteristics of 177Lu-DOTA-gluBBN

An experiment for confirming internalization characteristics of 177Lu-DOTA-gluBBN prepared according to Example 2 into the PC-3 cells was performed. After reacting 177Lu-DOTA-gluBBN (25,000 CPM) in the PC-3 cells, which are human prostate cancer cells, at 37° C., reaction solutions after 15, 30, 60, and 120 minutes were recovered, respectively. After the cells were washed with PBS, and the radioactive nuclide attached to the cell membrane was recovered using an acetic acid solution (pH 2.5). The radioactive nuclide internalized in the cells was recovered using a 1N NaOH solution, and radioactivity of each solution was measured using a gamma counter.

Figure 3:
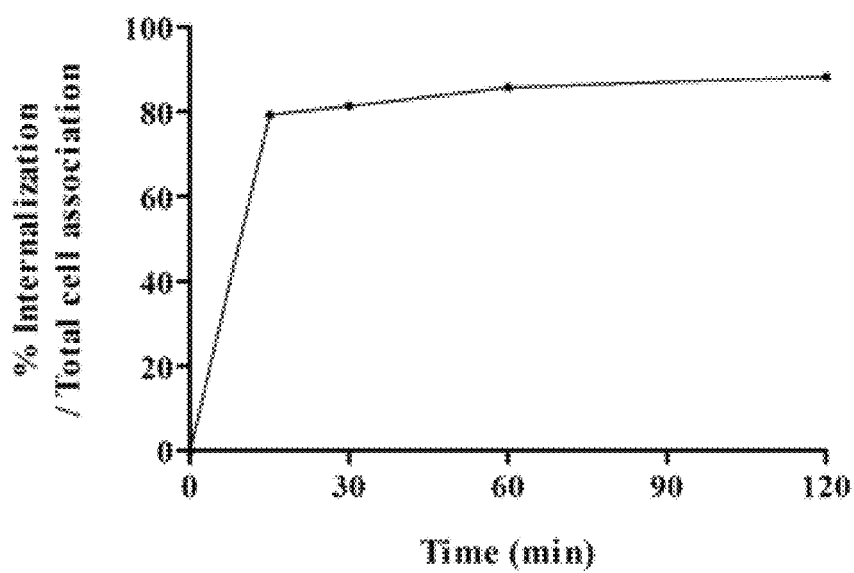
FIG. 3 is a graph showing an internalization result of 177Lu-DOTA-gluBBN in human prostate cancer PC-3 cells.

The result was shown in FIG. 3. As a result, 80% or more of 177Lu-DOTA-gluBBN was internalized in the PC-3 cells within 30 minutes, such that the radioisotope remained in the cells. Therefore, 177Lu-DOTA-gluBBN is useful for diagnosing and treating prostate cancer.

EXAMPLE 5

In Vivo Targeting Efficiency of 177Lu-DOTA-gluBBN to Prostate Cancer

In order to evaluate in vivo targeting efficiency of 177Lu-DOTA-gluBBN, in vivo distribution of 177Lu-DOTA-gluBBN in a tumor mouse model obtained by xenografting PC-3 cells, which are human prostate cancer cells, into a Balb/c nude mouse (Nara biotech, Korea) was evaluated. The tumor-bearing mouse model was prepared by subcutaneously injecting the PC-3 cells ($1 \times 10^7$) into a right upper end of the shoulder of a male Balb/c nude mouse (7 weeks old) and allowing tumor to grow for 3 weeks. 177Lu-DOTA-gluBBN (370 KBq) was intravenously injected into a tail vein of the tumor mouse model. After 1.5 hours of injection, the experimental animal was euthanized. Then, after the blood, the liver, the kidney, the spleen, the heart, the large intestine, the small intestine, the lung, the stomach, the pancreas, and the like, in addition to the tumor were extracted, weights of the organs were measured, and radioactivity of each organ was measured. 177Lu-DOTA-gluBBN uptake in each organ was expressed as percentage of the injected dose per unit weight (% ID/g). It was confirmed that 177Lu-DOTA-gluBBN targeted prostate cancer cells at 1 hour after intravenous injection with high efficiency (12.42±2.15% ID/g). The result was shown in FIG. 4.

EXAMPLE 6

Comparison of In Vivo Targeting Efficiency to Prostate Cancer with Comparative Material Having Similar Mechanism As a material having prostate cancer targeting mechanism similar to that of the bombesin derivatives (177Lu-DOTA-gluBBN) using the bombesin derivatives, which is the GRP-R agonist, prepared according to Example 2, 177Lu-AMBA (comparative material (J. Nucl. Med. 47(7):1144-1152 (Non-Patient Document)), see compound in FIG. 1) is a prostate cancer targeting diagnosis and treatment material of which excellent targeting efficiency is recognized, such that currently a phase 1 clinical trial was terminated. At the time of comparing in vivo targeting efficiency of the comparative material and 177Lu-DOTA-gluBBN according to Example 2 of the present invention to prostate cancer with each other, targeting efficiency of 177Lu-DOTA-gluBBN to prostate cancer was 1.95 times higher than that of 177LU-AMBA, which is the comparative material, and 177Lu-DOTA-gluBBN was more rapidly removed in the blood, such that it was proved from the result shown in FIG. 5 that 177Lu-DOTA-gluBBN had an improved effect as the bombesin derivatives.

EXAMPLE 7

In Vivo Imaging Diagnosis Efficiency of 177Lu-DOTA-gluBBN

Figure 6:
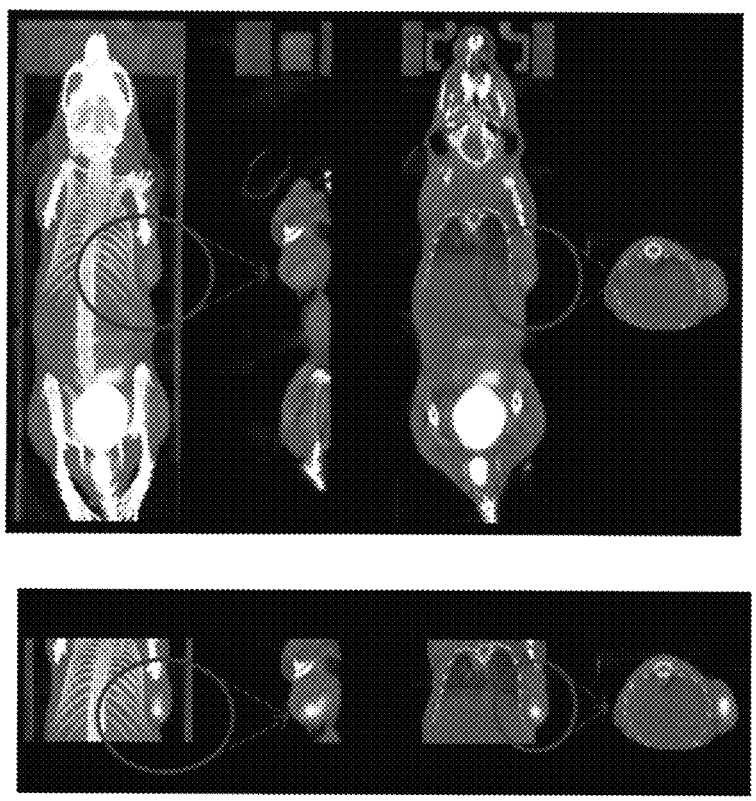
FIG. 6 is a result showing in vivo imaging diagnosis efficiency of 177Lu-DOTA-gluBBN.

In order to evaluate imaging diagnosis efficiency of 177Lu-DOTA-gluBBN prepared according to Example 2 in an animal model, a tumor mouse model in which human PC-3 cells were xenografted into a right shoulder portion thereof was used. At the time of photographing a single-photon emission computed tomography-compute tomography (SPECT-CT) image in the tumor mouse model after 1 hour of intravenous injection of 177Lu-DOTA-gluBBN (27.75 MBq) into a tail vein of the tumor mouse model, a tumor site formed in tumor mouse model may be accurately diagnosed using 177Lu-DOTA-gluBBN. The result was shown in FIG. 6.

EXAMPLE 8

Figure 7:
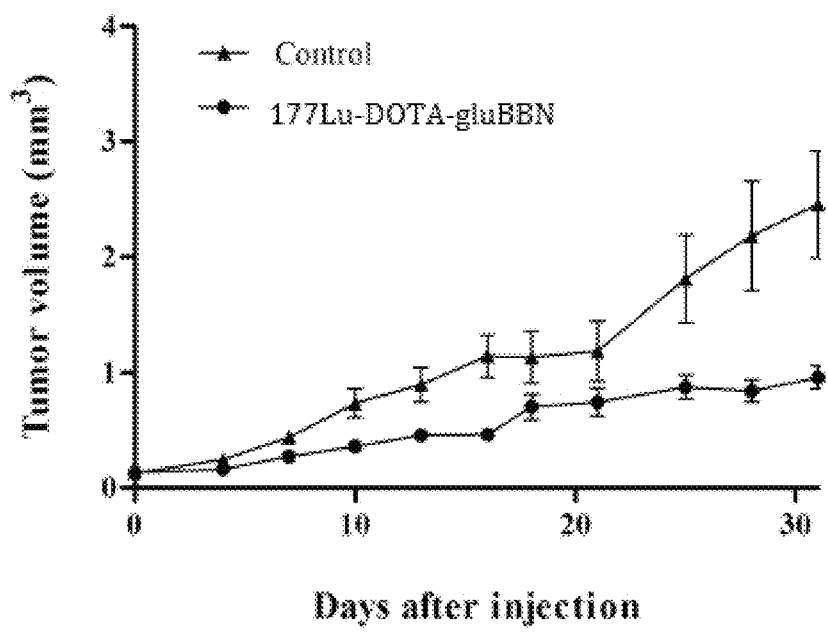
FIG. 7 is a graph showing therapeutic efficiency of 177Lu-DOTA-gluBBN to human prostate cancer.
Figure 7:
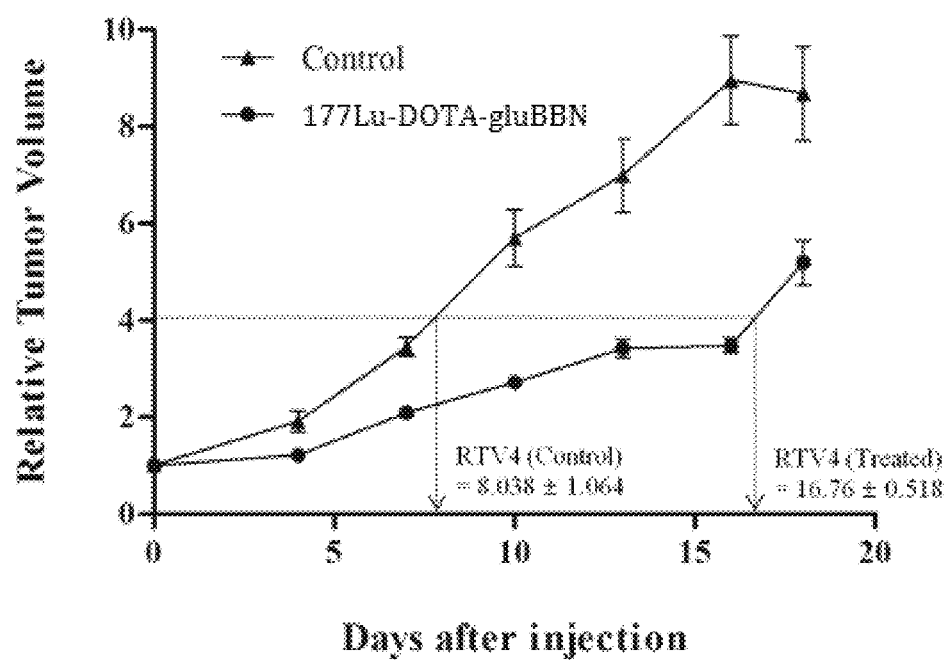

In Vivo Therapeutic Efficiency of 177Lu-DOTA-gluBBN (1) In Vivo Anti-Tumor Effect In order to evaluate therapeutic efficiency of 177Lu-DOTA-gluBBN prepared according to Example 2 in an animal model, a tumor mouse model in which human PC-3 cells were xenografted into a right shoulder portion thereof was used. At the time of intravenously injecting 177Lu-DOTA-gluBBN (27.75 MBq) 2 times into a tail vein of the tumor mouse model every 14 days and measuring a tumor volume, 177Lu-DOTA-gluBBN may significantly suppress a growth rate of tumor formed in the tumor mouse model. In addition, a value of a relative tumor volume×4 (RTV4), which is a time until a tumor volume became 4 times a tumor volume at the time of administration, was calculated, and as a result, RTV4 was increased about 2 times as compared to a control group. The result was shown in FIG. 7.

(2) Evaluation of In Vivo Physiological Toxicity of 177Lu-DOTA-gluBBN

Figure 8:
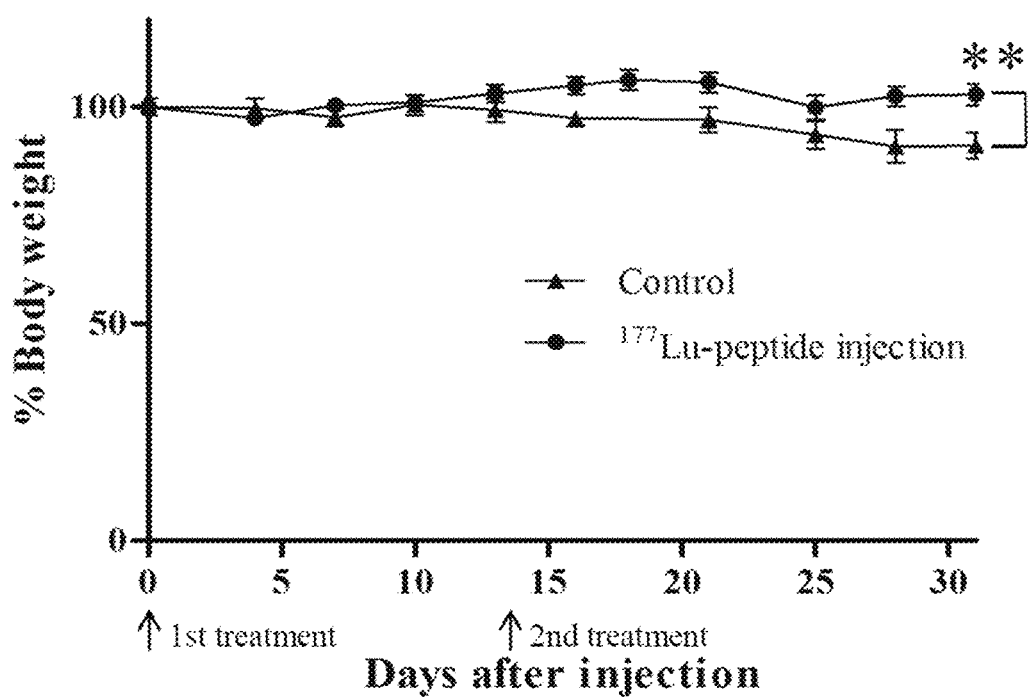
FIG. 8 is a graph showing an evaluation result of in vivo physiological toxicity of 177Lu-DOTA-gluBBN.

In order to confirm a toxicological effect by therapeutic dose, a body weight and histological states of organs were evaluated. The body weight was measured twice a week, and after euthanizing the animal model at the timing at which evaluation was terminated, spleen and kidney tissue was collected and H&E stained. In a control group, as the xenografted tumor grew, the body weight was decreased, but in an administration group, there was not a great change in the body weight at an early stage of administration. The result was shown in FIG. 8.

(3) Evaluation of In Vivo Histological Toxicity of 177Lu-DOTA-gluBBN

Figure 9:
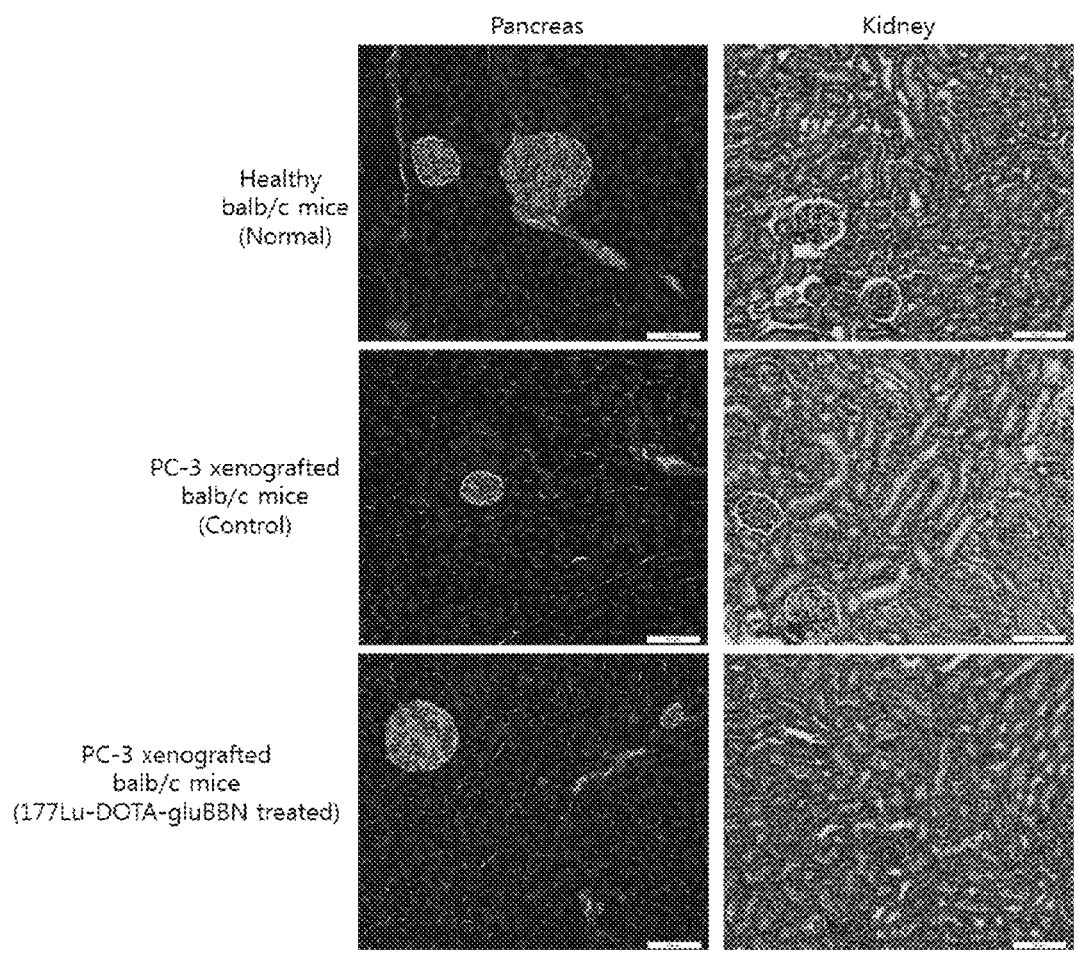
FIG. 9 is a photograph showing an evaluation result of in vivo histological toxicity of 177Lu-DOTA-gluBBN.

At the time of collecting spleen and kidney tissue in which toxicity may be exhibited by radioactivity and comparing the collected spleen and kidney tissue with those of a healthy Balb/c nude mouse (normal) that was not xenografted with cancer cells and a control group xenografted with cancer cells, histological toxicity by injection of 177Lu-DOTA-gluBBN was not observed. The result was shown in FIG. 9.

What is claimed is:

1. A bombesin derivatives represented by the following Chemical Formula 2:

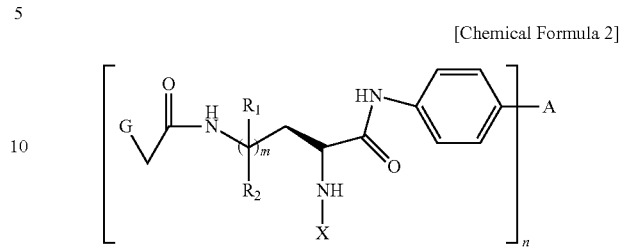

[Chemical Formula 2]

[In Chemical Formula 2,
n is an integer of 1 to 3,
m is an integer of 1 to 5,
$R_1$ and $R_2$ are each independently hydrogen or [c1-c5] alkyl,
X is a metal chelator and G is a glucose group or derivatives thereof,] and
A: *-Gln-Trp-Ala-Val-Gly-His-Leu-Met-NH$_2$.

2. The bombesin derivatives of claim 1, wherein X includes one or more radioactive metal nuclides and is a metal chelator for a trivalent metal.

3. The bombesin derivatives of claim 2, wherein the metal chelator for the trivalent metal is a DOTA-based chelator.

4. The bombesin derivatives of claim 2, wherein the radioactive metal nuclide is for radiotherapy and is selected from the group consisting of $^{176}$Yb, $^{111}$In, $^{169}$Gd, $^{177}$Lu, $^{105}$Rh, $^{111}$Ag, $^{64}$Cu, $^{67}$Ga, $^{68}$Ga, $^{125}$I, $^{123}$I, $^{129}$I, and $^{166}$Ho.

5. The bombesin derivatives of claim 1, wherein in Chemical Formula 2, n is 3 and $R_1$ and $R_2$ are hydrogen.

6. The bombesin derivatives of claim 1, wherein in G is

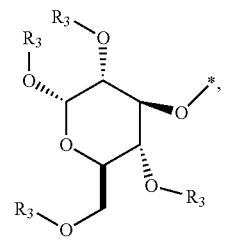

$R_{3(s)}$ are each independently hydrogen or a hydroxyl protecting group.

7. A preparation method of a bombesin derivatives comprising synthesizing a compound represented by the following Chemical Formula 2:

---

SEQUENCE LISTING

<160> NUMBER OF SEQ ID NOS: 1

<210> SEQ ID NO 1
<211> LENGTH: 8
<212> TYPE: PRT
<213> ORGANISM: Bombina bombina

<400> SEQUENCE: 1

Gln Trp Ala Val Gly His Leu Met
 1               5

[Chemical Formula 2]

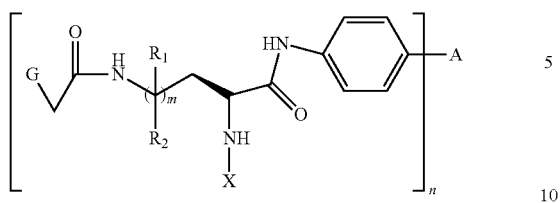

[In Chemical Formula 2,
n is an integer of 1 to 3,
m is an integer of 1 to 5,
X is a metal chelator,
$R_1$ to $R_2$ are each independently hydrogen or (C1-C5) alkyl,
A is *-Gln-Trp-Ala-Val-Gly-His-Leu-Met-NH2, and
G is a glucose group or derivatives thereof].

8. A composition for diagnosis and treatment of diseases associated with the prostate comprising the bombesin derivatives of claim 1.

* * * * *